United States Patent [19]

Lemon

[11] Patent Number: 4,937,238
[45] Date of Patent: Jun. 26, 1990

[54] PREVENTION OF MAMMARY CARCINOMA

[75] Inventor: Henry M. Lemon, Omaha, Nebr.

[73] Assignee: The Board of Regents of the University of Nebraska, Lincoln, Nebr.

[21] Appl. No.: 253,358

[22] Filed: Sep. 30, 1988

Related U.S. Application Data

[63] Continuation of Ser. No. 836,104, Mar. 4, 1986, abandoned.

[51] Int. Cl.$^5$ ............................................. A61K 31/56
[52] U.S. Cl. ..................................... 514/178; 514/182
[58] Field of Search .............................. 514/178, 182

[56] References Cited

U.S. PATENT DOCUMENTS 3,868,452  2/1975  Kraay et al. ....................... 514/182

OTHER PUBLICATIONS

The Merck Index; 10th Ed. (1983); #3579, Equilenin.
Chemical Abstracts; vol. 100 (1984) #186065M; Dehennin et al.
Chemical Abstracts; vol. 101 (1984) #488096; Leclercq et al.
Chemical Abstracts; vol. 101 (1984) #48830b; Katzenellenbogen.

*Primary Examiner*—Joseph A. Lipovsky
*Attorney, Agent, or Firm*—Vincent L. Carney

[57] ABSTRACT

To reduce the risk of breast cancer, a drug is periodically administered to young mammals before pregnancy in doses of about 1 microgram to 50 micrograms per kilogram of body weight. The drug: (1) competes with and displaces estradiol 17 beta from the mammary gland cells in an effective manner to prevent the possible formation of DNA-damaging epoxide estradiol metabolites; (2) binds to breast tissue to a greater extent than estradiol 17 beta; (3) induces terminal nonlactation differentiation of the mammary gland; (4) is nontoxic and noncarcinogenic; and (5) preferably does not cause anti-ovulatory activity. The drug is selected from a group of drugs including: (1) 4-OH estradiol; (2) d-equilenin; and (3) 17 alpha ethynyl estriol.

5 Claims, No Drawings

PREVENTION OF MAMMARY CARCINOMA

This application is a continuation of application Ser. No. 836,104 filed Mar. 4, 1986, now abandoned.

BACKGROUND OF THE INVENTION

This invention relates to drugs for reducing the risk of breast cancer and methods of using them.

It is known that the risk of breast cancer is related to pregnancy and that certain estrogen compounds affect the risk of cancer. Such compounds have been administered to mice and to women.

One compound that has been tested is estriol as described in "Estriol Prevention of Mammary Carcinoma Induced by 7, 12-dimenthylbenzanthracene and Procarbazine" by Henry M. Lemon, *Cancer Research*, 35, 1341–1353, May 1975. Estriol, a naturally occurring major human pregnancy hormone, was shown in that article to be moderately effective in inhibiting the development of breast cancers induced by a carcinogenic chemical.

Two other compounds and their method of use were described in "Pathophysiologic Considerations in the Treatment of Menopausal Patients with Oestrogens; the Role of Ostriol in the Prevention of Mammary Carcinoma" by Henry M. Lemon, *Acta Endocrinologica*, 1980, Suppl. 233:17–27. Those drugs are 6 keto estradiol and estriol 3-methyl ether. They were shown to have a 30–50 percent lifetime effect in reducing the appearance of breast carcinoma in treated rats as compared to other rats receiving carcinogen at the same time.

In one test: (1) 26 percent of the rats developed cancer in 7 months and 63 percent in one year when treated with estriol and a carcinogen; and (2) 31 percent of rats developed cancer in 7 months and 61 percent in one year when treated with 6 keto estradiol. Several other related drugs tested at the same did not provide the same beneficial results.

In tests with the other drugs the rats: (a) were treated with the drug and the carcinogen; and (b) examined for percentage incidence of cancer at 7 months and one year. Some of the other drugs in the test and their results were: (1) tamoxifen with 78 percent incidence in 7 months and 89 percent in one year; (2) diethylstilbestrol with 88 percent incidence in 7 months and 100 percent in one year; (3) 17 alpha ethynyl estradiol 17 beta with 90 percent in 7 months and 100 percent in one year; and (4) 2-OH estradiol 17 beta with 78 percent in 7 months and 94 percent in one year.

The three drugs which were effective and the methods of treatment using them have the disadvantages of low effectiveness and/or toxicity.

It is known to increase retention in uterus tissue by conjugating drugs with 17 alpha ethynyl which has a high rate of retention in uterus nuclei. Moreover, estrogen, 11-beta methoxy 17 alpha ethynyl estradiol 17 beta, which is retained in breast tissue, is known in biochemical studies of breast cancer tissue. However, this estrogen has the disadvantage of being carcinogenic in animals. It is also known that some estrogens cause cell transformation in tissue culture.

SUMMARY OF THE INVENTION

It is an object of the invention to provide a novel method for preventing breast cancer.

It is a further object of the invention to provide a novel drug for the prevention of breast cancer.

It is a still further object of the invention to provide a novel method of reducing the risk of breast carcinoma using a drug with minimum undesirable effects.

It is a still further object of the invention to provide a method for reducing the risk of breast cancer through the use of a drug which does not inhibit ovulation, uterine hypertrophy, or body growth.

It is a still further object of the invention to provide a method of reducing the risk of breast cancer through treatment with a drug not having cell transforming activity or exhibiting damage to DNA.

In accordance with the above and further objects of the invention, a hormone or a drug which creates a hormone is induced in young female mammals in a dosage which competes with and displaces cell transforming hormones to prevent the formation of DNA-damaging epoxides from hormone metabolites and induces pre-lactational terminal differentiation of the mammary gland in sufficient quantities to reduce the incidence of carcinoma in undifferentiated cells which might otherwise be caused by other natural occurring hormones. The drug is administered in quantities which do not have undesirable effects on the mammal such as the inhibition of ovulation or inhibiting of growth.

Preferably, the drug is one with long retention time within the breast tissue at the effective dosage. Small doses are applied between 1 ug (micrograms) for each kilogram of body weight and 50 ug for each kilogram of body weight between the ages in humans of 15 years to 20 years.

As an active ingredient, the drug is selected from a group of drugs including: (1) 4-OH estradiol; (2) d-equilenin; and (3) 17 alpha ethynyl estriol. The most satisfactory of these drugs is believed at this time to be 17 alpha ethynyl estriol. The drugs d-equilenin and 4-OH estradiol may be conjugated with 17 alpha ethynyl to increase their effectiveness and/or reduce the dose.

At first testing, 17 alpha ethynyl estriol appeared not to have anti-mammary carcinogenic activity but in this test the 17 alpha ethynyl estriol was administered within 2 to 3 days of administering a carcinogen to the same rats and it is believed that the ethynyl estriol provided stimulation of cell proliferation during the time of the maximum damage by the carcinogen resulting in increased cancer. Subsequent testing which avoided the large scale proliferation of DNA damaged cells has shown ethynyl estriol to be effective in rats.

As can be understood from the above summary of the invention, the method of treatment and drugs of this invention have several advantages, such as: (1) they reduce the risk of esdridial dependent mammary carcinoma; (2) they do not inhibit body growth; (3) they do not inhibit ovulation; (4) they do not stimulate prolactin induction of secretory activity in the mammary gland; (5) they have a high maturation activity for immature mammary glands; and (6) they do not cause uterine hypertrophy.

DETAILED DESCRIPTION

Broadly, the drug is a hormone or compound which causes production of the hormone in mammals, including humans, which hormone or compound: (1) does not transform cells into malignant cell clones; (2) competes with and displaces cell-transforming hormones; (3) prevents the formation of DNA-damaging epoxides from hormone metabolites; (4) induces prelactational terminal differentiation of the mammary gland; (5) is retained for a substantial amount of time in breast tissue; and (6) has minimum undesirable effects. Preferably it should not induce lactation when administered in the quantities used to reduce the risk of cancer.

More specifically, the hormone should: (1) compete with and displace estradiol 17 beta from the mammary gland cells in an effective manner to prevent the possible formation of DNA-damaging epoxide estradiol metabolites; (2) bind to breast tissue to a greater extent than estradiol 17 beta; (3) induce terminal differentiation of the mammary gland; (4) be nontoxic and noncarcinogenic; and (5) preferably not have anti-ovulatory activity. The treatment may also be used in larger quantities as a combined cancer preventative means and contraceptive. The drug is selected from a group of drugs including: (1) 4-OH estradiol; (2) d-equilenin; and (3) 17 alpha ethynyl estriol. The drug is preferably 17 alpha ethynyl estriol.

Suitable compounds: (1) have the general formula shown in formula 1 where R2 is a hydroxy group, R8 is an oxygen function comprising a 16 alpha hydroxy group or a keto group (=O), R1, and R9-R11 are hydroxy groups or nonreactive hydrogen groups and R7 is a methyl group; or (2) have the general formula shown in formula 2 where R2 is a hydroxy group and R1 and R9-R11 are hydroxy groups or nonreactive hydrogen groups, R7 is a methyl group, and R8 may be a 17 beta hydroxy group. In either formula 1 or 2: (1) R8 can be a 17 alpha hydroxy group and (2) R4 is a non-reactive hydrogen. The general structures of formulae 1 and 2 will resemble the peripheral structures of ethynyl estriol, d-equilenin, and 4-OH estradiol. Formula 1 identifies the four rings by using a convention that will be followed throughout this specification.

To provide significant cancer inhibition, a proper dose is between 2 ug (micrograms) each 24 hours for 28 days and 1 ug each 24 hours for 84 days. A single 638 ug dose provides a full year of protection, as does the 1.0 ug/24 hour dose, something not yet demonstrated as well for any other estrogen.

Five specific suitable active ingredients are: (1) 17 alpha ethynyl estriol shown in formula 3; (2) 4-OH estradiol 17 beta shown in formula 4; (3) d-equilenin shown in formula 6, (4) 17 alpha ethynyl 4-OH estradiol 17 beta; and (5) 17 alpha ethynyl d-equilenin.

Some of the specific compounds which are the active ingredient in the dose administered to patients for prevention of mammary carcinogenesis are known compounds and are not part of this invention in general. Ethynyl estriol is obtainable from Eli Lilly, Inc., Greenfield, Ind., and the other estrogens from Sigma, Inc., St. Louis, Mo., or Steraloids, Inc., Wilton, N.H.

Generally, the compounds are estrogens which have an additional oxygen function (=O, or —OH) on the bottom and right side of the molecule (R1, R2 or D ring) and R8-R9 or A ring of the molecules, or would be expected to undergo selective oxidation at this part of the molecule in the tissues in vivo. For example, (1) estriol, ethynyl estriol, 4-OH estradiol, 6-keto estradiol have this oxygen function; (2) moxestrol can only be oxidized in vivo at the 4C position, since the ethynyl group blocks 16 beta oxidation, and the 11 beta-methoxy group blocks 2-hydroxylation and R3; and (3) d-equilenin has been shown to be oxidized in vitro by tissues almost exclusively at the C4 (R1) position.

Young virgin female mammals have the drug of this invention administered to them either in one large dose or periodically to reduce the risk of breast cancer. It is administered in sufficient quantity to compete with and displace hormones which are likely to induce cell transformation and their metabolites, and to increase the speed of differentiation of the mammary gland cells but in small enough quantities to avoid undesirable effects.

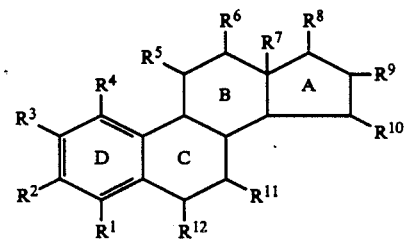

FORMULA 1

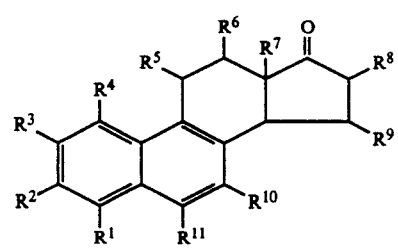

FORMULA 2

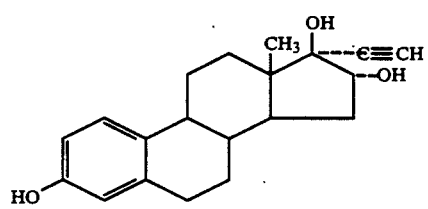

FORMULA 3

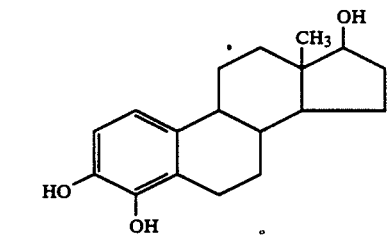

FORMULA 4

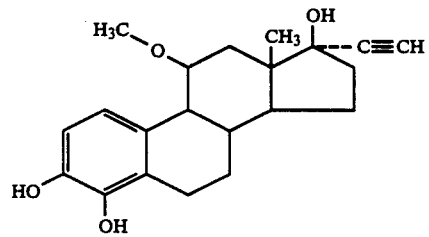

FORMULA 5

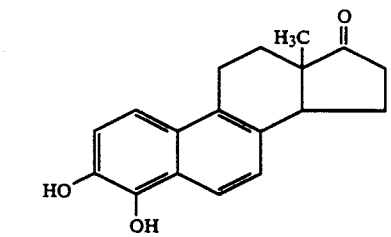

FORMULA 6

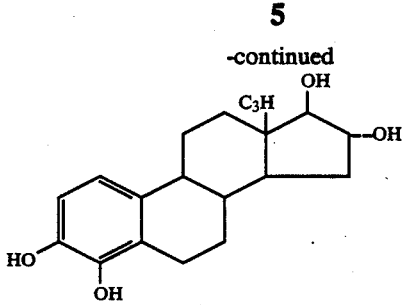

FORMULA 7

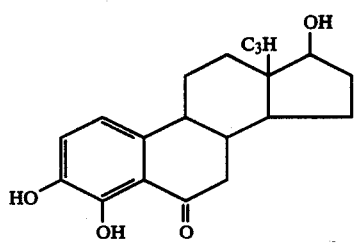

FORMULA 8

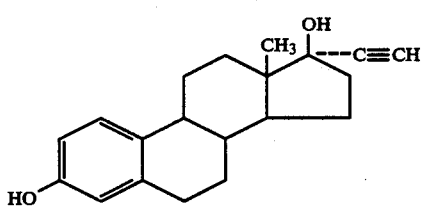

FORMULA 9

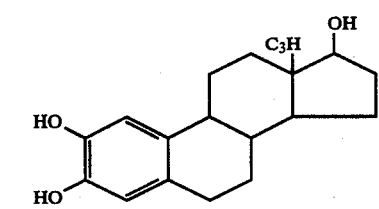

FORMULA 10

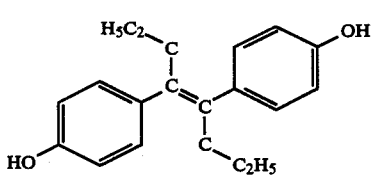

FORMULA 11

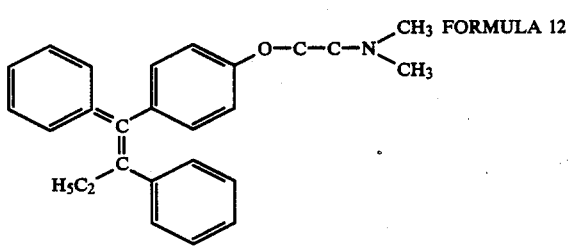

FORMULA 12

Generally, drugs which compete with and displace estradiol 17 beta from mammary gland cells and prevent the possible formation of DNA-damaging epoxides from estradiol metabolites are used in sufficient quantities to increase pre-lactational differentiation of the post-pubertal mammary gland cells. They are administered to female humans at ages younger than 20 and prior to pregnancy, usually in periodic doses. This treatment may be most useful soon after (within five years in the case of humans) the onset of menarche and the date of pregnancy in doses and quantities too small to induce lactation or toxicity.

The invention is illustrated by the following non-limiting examples:

EXAMPLES

General

In tests for anti-mammary carcinogenic activity following the feeding of carcinogen to mammals, ten different estrogenic compounds were implanted in female rats fed a carcinogen. The incidence of breast cancer for each compound was determined. Rats receiving only the carcinogen were used as controls. Ethynyl estriol was obtained from Eli Lilly, Inc., Greenfield, Indiana; the other estrogens were obtained from Sigma, Inc., St. Louis, Mo., or Steraloids, Inc., Wilton, N.H.

Rats and their Maintainence

In all of the tests, intact female Sprague-Dawley rats, obtained from Sasco, Inc., Omaha, Nebr., at 50 to 55 days of age were used.

They were: (1) randomized upon receipt; (2) housed individually in suspended cages; (3) fed Purina Lab Chow and distilled water; and (4) the temperature was maintained within 22-23 degrees and 40-50 percent relative humidity.

Formation of Pellets

The hormones were formed into pellets weighing 6.38SD mg (milligrams) having 1 millimeter diameters and being between 1 and 2 millimeters in length, generally being cylindrical in shape. Each pellet contained 5-10 percent of the hormone to be administered in crystalline sodium chloride w/w (The weight of the hormone was 5-10 percent of the total weight of the pellets.). The pellets were compressed into solid form using a Forbes manual pellet press as described in Forbes, T. R., "Absorption of Pellets of Crystalline Testosterone, Testosterone Propionate, Methyl Testosterone, Progesterone, Desoxycorti-costerone, and Stilbestrol Implanted in the Rat." *Endocrinology*, 29: 7071, 1941.

Hormones

The hormones used in examples 1-10 are shown in formulas 3-12 respectively and are: (1) 17 alpha ethynyl estriol shown in formula 3; (2) 4—OH estriadiol 17 beta shown in formula 4; (3) 11 beta methoxy 17 alpha ethynyl estradiol 17 beta shown in formula 5; (4) d-equilenin shown in formula 6; (5) estriol shown in formula 7; (6) 6-keto estradiol 17 beta shown in formula 8; (7) 17 ethynyl estradiol 17 beta shown in formula 9; (8) 2-hydroxy estradiol 17 beta shown in formula 10; (9) diethylstilbestrol shown in formula 11; and (10) tamoxifen shown in formula 12. The ethynyl estriol was obtained from Ely Lilly, Inc., Greenfield, Ind., moxestrol was obtained from Southwest Foundation for Biomedical Research in San Antonio, Tex., and the remainder of the hormones were obtained either from Sigma, Inc., St. Louis, Mo. or Steraloids, Inc., Wilton, N.H.

Carcinogen

The carcinogen DMBA (7, 12-dimethylbenz (a) anthracene) was obtained from Eastman Kodak Co., Rochester, N.Y., and was dissolved in sesame oil immediately before administration, in a concentration of 20 mg for each 1.5 ml of oil for each dose.

Administration of DMBA

DMBA was administered under light ether anesthesia using a flexible 12 cm garage tube.

Administration of Hormones

Hormonal treatment of one-half to two-thirds of each batch of age-matched rats was begun 14–21 days prior to DMBA therapy or 13–14 days following DMBA therapy. Two methods were used, hereinafter referred to as: (1) pellet method; and (2) minipump method.

Pellet Method

Pellets were implanted monthly, subcutaneously. The dynamics of release from such pellets has been described by Forbes, T. R. in "Further Observation on the Relative Absorption Rates of Pellets of Various Crystalline Compounds Implanted Subcutaneously in Rats,-" i Endocrinology," 30:761–769, 1942.

Minipump Method

Alzet Osmotic Minipumps from Alzet Corporation in California were s.c. (subcutaneously) implanted in each rat and the designated hormone dose was pumped contained in a vehicle composed of 5 percent ETOH, 25 percent distilled water and 70 percent propylene glycol.

Experiment Design

The randomized rats were divided into groups of 4–15 rats each and each group was assigned to a different one of: (1) untreated controls; (2) carcinogen-treated rats; and (3) carcinogen-untreated rats.

The rats were examined for neoplasm every 10 to 14 days after feeding DMBA. At least one mammary neoplasm was verified pathologically in each tumor-bearing rat which was killed at the time of biopsy. Wet and dry uterine weights were obtained at necropsy.

Rats free of neoplasms were followed for one year. At the end of the one year, the remaining rats were necropsied. Non-neoplastic mammary glands were also biopsied at necropsy to obtain evidence of estrogenic stimulation of the virgin ductal system. Significant differences in cancer incidence between treated and controlled groups were determined.

Calculations of Differences in Cancer Incidence

The differences in cancer incidence between treated and controlled groups in each experiment were determined by $X^2$ using the Yate's correction. When the number of rats was small, the Fisher exact probability test for four-fold tables with cells containing less than five rats was used. The significance of difference in mammary-carcinoma-free survival in rate-days was determined for these groups at 210 days after DMBA administration using the Mann-Whitney U Test. Differences in mean values of uterine weights were evaluated using Students t test of significance.

EXAMPLE ONE

Ethynyl Estriol

The ethynyl estriol was administered either two to three weeks before DMBA feeding or two weeks after. The results of this treatment are shown in Tables 1–5, 9 and 10.

EXAMPLE TWO

Tamoxifen

Tamoxifen was administered in doses of 1.5 to 2.5 mg each month starting 13 to 14 days after feeding DMBA. The results of this treatment are shown in Table 6.

EXAMPLE THREE

Diethylstibestrol

Diethylstibestrol was administered in doses of micrograms each month starting 13 to 14 days after feeding DMBA. The results of this treatment are shown in Table 6.

TABLE 1

INHIBITION OF MAMMARY CARCINOGENESIS BY ETHINYL ESTRIOL PRIOR TO CARCINOGEN

| | Mammary Carcinoma Incidence | | | | | |
|---|---|---|---|---|---|---|
| | CONTROLS Ratio of rats with carcenogenesis to total rats observed | | ETHINYL ESTRIOL Ratio of rats with carcenogensis to total rats observed | | SIGNIFICANT DIFFERENCE | |
| Treatment Dosage and time of administration | after 210 days | after 365 days | after 210 days | after 365 days | U method | $X^2$ method |
| 638 ug monthly for 7 months starting at 35 d (days) of age (14 days before DMBA) | 8/10 | 9/10 | 0/8 | 1/8 | <.001 | <.001 |
| 638 ug implanted at 50 days of age (21 days before DMBA) continuous infusion starting at 35 days of age (15 days before DMBA) | 7/11 | | 1/13 | 5/13 | <.05 | none |
| 2 ug/24 h (hrs) × 28 d | 11/12 | 11/12 | 6/12 | | <.02 | |
| 6 ug/24 h × 28 d | | | 5/12 | | <.001 | |

TABLE 2

INHIBITION OF MAMMARY CARCINOGENESIS BY ETHINYL ESTRIOL TWO WEEKS AFTER CARCINOGEN

| | Mammary Carcinoma Incidence | | | | | |
|---|---|---|---|---|---|---|
| | CONTROLS Ratio of rats with carcenogenesis to total rats observed | | ETHINYL ESTRIOL Ratio of rats with carcenogensis to total rats observed | | SIGNIFICANT DIFFERENCE | |
| Treatment | | | | | | |
| Dosage and time of administration | after 210 days | after 365 days | after 210 days | after 365 days | U method | $X^2$ method |
| 638 ug monthly × 19 | 9/12 | 10/12 | 0/11 | 9/11 | <.001 | none |
| 638 ug monthly × 7 | 14/14 | 14/14 | 1/15 | 5/15 | <.001 | <.02 |
| continuous infusion 1 ug/24 h × 84 d | 9/12 | 12/12 | 4/9 | 5/9 | none | <.025 |
| 638 ug implanted once | 7/11 | | 1/12 | | <.05 | |

TABLE 3

UTERINE WEIGHTS OBTAINED AT THE TIME OF NECROPSY FOR NEOPLASMS (IN GRAMS)

| | HORMONE-TREATED | | CONTROLS | | |
|---|---|---|---|---|---|
| Treatment | Number of Rats | Wet Uterine Weight | Number of Rats | Wet Uterine Weight | Significant Difference |
| monthly EE3 pellet implants | 7 | .452 ± .071 | 15 | .526 ± .139 | none |
| monthly EE3 pellet implants | 4 | .513 ± .076 | 10 | .530 ± .119 | none |
| single EE3 pellet at age 50 d. | 5 | .661 ± .122 | 9 | .547 ± .159 | none |
| 2 ug/24 h infused 28 d | 8 | .471 ± .136 | 12 | .534 ± .124 | none |
| 6 ug/24 h infused 28 d | 7 | .546 ± .090 | 12 | .534 ± .124 | none |

TABLE 4

UTERINE WEIGHTS OBTAINED AT THE END OF HORMONAL STIMULATION

| | HORMONE-TREATED | | CONTROLS | | |
|---|---|---|---|---|---|
| Treatment | Number of Rats | Wet Uterine Weight | Number of Rats | Wet Uterine Weight | Significant Difference |
| 1.2 ug/24 h infused 28 days | 1 | .426 | 1 | .452 | −6 |
| 2.0 ug/24 h infused 28 days | 2 | .502 | 2 | .341 | +47 |
| 3.4 ug/24 h infused 28 days | 1 | .556 | 1 | .323 | +42 |
| 6.0 ug/24 h infused 28 days | 2 | .592 | 2 | .341 | +74 |
| 6.0 ug/24 h infused 28 days | 1 | .683 | 1 | .339 | +101 |
| 2.0 ug/24 h infused 28 days | 2 | .791 | 2 | .341 | +132 |
| 6.0 ug/24 h infused 28 days | 2 | .925 | 2 | .341 | +172 |

(all of the above variations in weight are within the normal spontaneous weight variations plus or minus 3 times the standard deviation X5D)

TABLE 5

UTERINE WEIGHTS OBTAINED AT THE END OF HORMONAL STIMULATION

| | HORMONE-TREATED | | CONTROLS | | |
|---|---|---|---|---|---|
| Treatment | Number of Rats | Wet Uterine Weight | Number of Rats | Wet Uterine Weight | Significant Difference |
| 30 d after 467 ug s.c. | 1 | .589 | 1 | .346 | +70 |
| 60 d after 645,469 ug s.c. each month | 1 | .604 | 1 | .620 | −3 |
| 60 d after 615,577 | 1 | .636 | 1 | .393 | +62 |
| untreated females 80 days of age | | | 4 | .423 | ±.102 |

(all of the above variations in weight are within the normal spontaneous weight variations plus or minus 3 times the standard deviation X5D)

TABLE 6

INFLUENCE OF OTHER ESTROGENS AND OF THE ANTI-ESTROGEN TAMOXIFEN UPON DMBA-INDUCED MAMMARY CARCINOGENSIS (ALL TREATMENT INITIATED 13-14 DAYS AFTER FEEDING DMBA)

| | Mammary Carcinoma Indicidence | | | | | |
|---|---|---|---|---|---|---|
| | CONTROLS Ratio of rats with carcenogenic to total rats and percentage with carcenogenic: | | TREATED Ratio of rats with carcenogenic to total rats and percentage with carcenogenic: | | SIGNIFICANT DIFFERENCE | |
| Treatment Dosage and time of administration | observed for 7 mos. | observed for 1 year | observed for 7 mos. | observed for 1 year | U method | $X^2$ method |
| Tamoxifen 1.5-2.5 mg/mo (month) | 18/19 (95%) | | 14/18 (78%) | 16/18 (89%) | none | none |
| Diethylstilbestrol 320 ug/mo | 10/10 (100) | | 7/8 (88) | 8/8 (100) | none | none |
| 17a ethynyl estradiol 17B 638 ug/mo × 7 mo | 14/14 (100) | | 9/10 (90) | 10/10 (100) | none | none |
| 2-OH estradiol 17B 638 ug/mo × 9 mo | 15/19 (79) | 18/19 (95) | 14/18 (78) | 17/18 (94) | none | none |

TABLE 7

INFLUENCE OF OTHER ESTROGENS AND OF THE ANTI-ESTROGEN TAMOXIFEN UPON DMBA-INDUCED MAMMARY CARCINOGENSIS (ALL TREATMENT INITIATED 13-14 DAYS AFTER FEEDING DMBA)

| | Mammary Carcinoma Indicidence | | | | | |
|---|---|---|---|---|---|---|
| | CONTROLS Ratio of rats with carcenogenic to total rats and percentage with carcenogenic: | | TREATED Ratio of rats with carcenogenic to total rats and percentage with carcenogenic: | | SIGNIFICANT DIFFERENCE | |
| Treatment Dosage and time of administration | observed for 7 mos. | observed for 1 year | observed for 7 mos. | observed for 1 year | U method | $X^2$ method |
| Estriol 638 ug/mo × 10 mo | 18/19 (95) | | 5/19 (26) | 12/19 (63) | <.001 | <.05 |
| 4-OH estradiol 638 ug/mo × 12 mo | 16/20 (80) | 19/20 (95) | 7/20 (35) | 13/20 (65) | <.001 | <.05 |
| 6-keto estradiol 638 ug/mo × 4 mo | 10/12 (83) | | 4/13 (31) | 8/13 (61) | <.01 | none |
| d-equilenin 638 ug/mo × 4 mo | 11/11 (100) | | 4/10 (40) | 4/10 (40) | <.001 | <.01 |

TABLE 8

INFLUENCE OF OTHER ESTROGENS AND OF THE ANTI-ESTROGEN TAMOXIFEN UPON DMBA-INDUCED MAMMARY CARCINOGENSIS (ALL TREATMENT INITIATED 13-14 DAYS AFTER FEEDING DMBA)

| | Mammary Carcinoma Indicidence | | | | | |
|---|---|---|---|---|---|---|
| | CONTROLS Ratio of rats with carcenogenic to total rats and percentage with carcenogenic: | | TREATED Ratio of rats with carcenogenic to total rats and percentage with carcenogenic: | | SIGNIFICANT DIFFERENCE | |
| Treatment Dosage and time of administration | observed for 7 mos. | observed for 1 year | observed for 7 mos. | observed for 1 year | U method | $X^2$ method |
| Moxestrol (11 beta methoxy 17a ethynyl 17B estradiol) 638-320 ug/mo × 11 mo | 21/30 | 26/30 | 3/29 | 14/29 | <.001 | <.05 |

EXAMPLE FOUR

Alpha Ethynyl Estradiol 17 Beta 17 alpha ethynyl estradiol 17 beta was administered in doses of 638 micrograms each month starting 13 to 14 days after feeding DMBA. The results of this treatment are shown in Table 6.

EXAMPLE FIVE

2-OH Estradiol 17 Beta

2-OH estradiol 17 beta was administered in doses of 630 micrograms each month for 9 months starting 13 to 14 days after feeding DMBA. The results of this treatment are shown in Table 6.

EXAMPLE SIX

Estriol

Estriol was administered in doses of 638 micrograms each month for 10 months starting 13 to days after feeding DMBA. The results of this treatment are shown in Table 6.

EXAMPLE SEVEN

4-OH Estradiol

4-OH estradiol was administered in doses of 638 micrograms each month starting 13 to 14 days after feeding DMBA. The results of this treatment are shown in Table 7.

EXAMPLE EIGHT

6-Keto Estradiol 6-keto estradiol was administered in doses of 638 micrograms each month starting 13 to 14 days after feeding DMBA. The results of this treatment are shown in Table 7.

EXAMPLE NINE

D-Equilenin d-equilenin was administered in doses of 638 ug (micrograms) each month starting 13 to 14 days after feeding DMBA. The results of this treatment are shown in Table 7.

EXAMPLE TEN

Moxestrol (17 Beta Methoxy 17 Alpha Ethynyl 17 Beta Estradiol)

Moxestrol (17 beta methoxy 17 alpha ethynyl 17 beta estradiol) was administered in doses of 638 to 320 micrograms each month starting 13 to 14 days after feeding DMBA. The results of this treatment are shown in Table 8.

TABLE 9

MAMMARY GLAND PROLIFERATIONS AND LACTATION INDUCED BY ETHYNYL ESTRIOL AND ETHYNYL ESTRADIOL 17

| Treatment | Mammary Alveolar Proliferations | Lactation |
|---|---|---|
| Continuous sub-cutaneous infusion by mini-pump into virgin 50 day old S-D females for 4 weeks: | | |
| Ethynyl estradiol 2 mg/d | ++ | + |
| Ethynyl estradiol 2 mg/d | +++ | + |
| Ethynyl estradiol 6 mg/d | ++ | + |
| Ethynyl estradiol 6 mg/d | ++++ | + |
| Ethynyl estriol 2 mg/d | +++ | 0 |
| Ethynyl estriol 2 mg/d | ++ | 0 |
| Ethynyl estriol 6 mg/d | ++ | 0 |
| Ethynyl estriol 6 mg/d | ++ | 0 |
| No treatment given | 0 | 0 |
| No treatment given | 0 | 0 |

(1 plus (+) barely detected; 4 pluses (+) up to 50% replacement of fat tissue by glands)

TABLE 10

ESTRUS CYCLES NOTED DURING A 21-DAY PERIOD OF ESTROGEN INFUSION

| Treatment | Number of Cycles/ 21 Days | |
|---|---|---|
| Ethynyl estradiol infused continuously | | |
| 2.0 mg/d | 0 | |
| 2.0 mg/d | 2 | mean 1/rat |
| 6.0 mg/d | 0 | |
| 6.0 mg/d | 2 | |
| Control - no infusions | 4 | mean 5/rat |
| Control - no infusions | 6 | |
| Ethynyl estriol infused continuously | | |
| 2.0 mg/d | 1 | |
| 2.0 mg/d | 3 | mean 2.5/rat |
| 6.0 mg/d | 2 | |
| 6.0 mg/d | 4 | |

Certain drugs such as 17 alpha ethynyl estriol reduce the risk of mammary carcinoma when administered in doses that do not have undesirable side effects even though other similar drugs are inactive or carcinogenic or toxic.

Although a preferred embodiment of the invention has been described in some detail, many modifications and variations are possible in the preferred embodiment without deviating from the invention. Accordingly, it is to be understood, that, within the scope of the appended claims, the invention may be practiced other than as specifically described.

What is claimed is:

1. A method of preventing breast cancer in female mammals comprising the steps of administering to the female mammal a compound which competes with and displaces cell-transforming hormones in the mammary gland without forming DNA-damaging epoxides from hormone metabolites in a dose of 1 microgram to 50 micrograms per kilogram of body weight once every 24 hours for 20 days for each month from between 3 to 6 months after the onset of menarche in sufficiently low dosages to avoid interfering with ovarium function, whereby the immature mammary glands are converted to mature differentiated cells in the glands without lactation; wherein the composition of matter administered is selected from the group of estrogen compounds comprising 4-hydroxy estradiol, 17 alpha ethynyl estriol and d-equilenin.

2. A method of preventing breast cancer in female mammals according to claim 1 in which the steps of administering to the female mammal a compound comprises administering the compound to human females between the age of 15 and 21 years.

3. A method according to claim 2 wherein the compound has the formula:

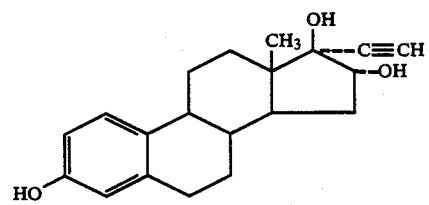

4. A method according to claim 2 wherein the compound has the formula:

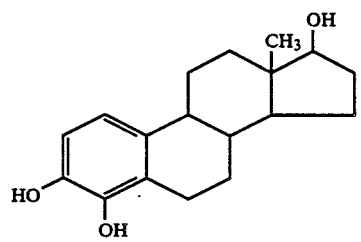
5. A method according to claim 2 wherein the compound has the formula:
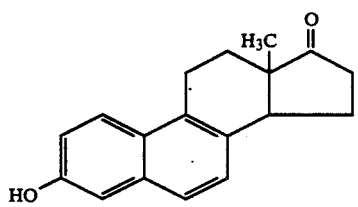
* * * * *